United States Patent [19]

Sauter et al.

[11] Patent Number: 4,822,889
[45] Date of Patent: Apr. 18, 1989

[54] TRIAZOLYL ALCOHOLS, THEIR PREPARATION AND THEIR USE AS FUNGICIDES

[75] Inventors: Hubert Sauter, Mannheim; Ludwig Schuster; Ernst-Heinrich Pommer, both of Limburgerhof; Eberhard Ammermann, Ludwigshafen, all of Fed. Rep. of Germany

[73] Assignee: BASF Aktiengesellschaft, Ludwigshafen, Fed. Rep. of Germany

[21] Appl. No.: 874,833

[22] Filed: Jun. 16, 1986

Related U.S. Application Data

[63] Continuation of Ser. No. 617,989, Jun. 6, 1984, abandoned.

[30] Foreign Application Priority Data

Jun. 10, 1983 [DE] Fed. Rep. of Germany ....... 3321023

[51] Int. Cl.$^4$ ............................................. C07D 249/12
[52] U.S. Cl. .................................. 548/262; 548/101
[58] Field of Search ......................................... 548/262

[56] References Cited

U.S. PATENT DOCUMENTS

| | | | |
|---|---|---|---|
| 4,117,229 | 9/1978 | Baker et al. | 548/301 |
| 4,232,033 | 11/1980 | Kramer et al. | 548/262 |
| 4,380,546 | 4/1983 | Sauter et al. | 548/101 |
| 4,456,608 | 6/1984 | Sauter et al. | 514/383 |

FOREIGN PATENT DOCUMENTS 0040350  4/1981  European Pat. Off. ............ 548/262

OTHER PUBLICATIONS

House, Modern Synthetic Reactions, 2nd edition, Benjamin/Cunnings Publishing Co., pp. 1–3.
Karrer, Organic Chemistry (2nd Ed., New York, 1946), pp. 96–97.

Primary Examiner—Glennon H. Hollrah
Assistant Examiner—Patricia L. Morris
Attorney, Agent, or Firm—Keil & Weinkauf

[57] ABSTRACT

Triazolyl alcohols of the formula

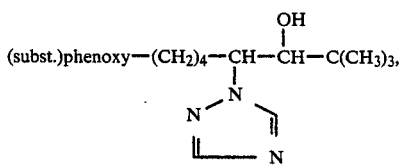

their addition salts with acids and their metal complexes, where the steroisomers are in certain ratios, the preparation of these compounds, the preparation of fungicides from these, and the use of these fungicides.

3 Claims, No Drawings

TRIAZOLYL ALCOHOLS, THEIR PREPARATION AND THEIR USE AS FUNGICIDES

This application is a continuation of application Ser. No. 617,989, filed on June 6, 1984, now abandoned.

The present invention relates to novel diastereomeric forms of triazolyl alcohols having the R*, S* configuration, a process for their preparation and their use as fungicides.

It is known that diastereomer mixtures of some triazolyl alcohols of the formula I possess fungicidal activity (cf. EP-No. 00 40 350). It has been found that these diastereomer mixtures each contain a very predominant amount of a diastereomer of the configuration R*, R*.

We have found triazolyl alcohols of the formula I

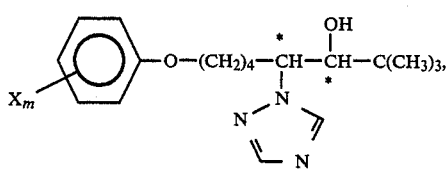

where X is hydrogen, halogen, trifluoromethyl, $C_1$–$C_4$-alkyl, $C_1$–$C_4$-alkoxy, unsubstituted or substituted phenyl or unsubstituted or substituted phenoxy and m is an integer from 1 to 5, X being identical or different where m is greater than 1, and the compounds, as diastereomers, having the R*, S* configuration at the two chiral centers, and have also found the enantiomers which have the configuration R,S or S,R at the two chiral centers.

The present invention furthermore relates to the acid addition salts and the metal complexes of the compounds of the formula I.

Compounds which have two different chiral carbon atoms form four stereoisomers whose configurations can be described using the Cahn-Ingold-Prelog system (cf. for example, D. Seebach and V. Prelog, Angew. Chem. 94 (1982), 696 and references stated therein). Of these isomers, two enantiomers having the configurations R,R and S,S constitute one diastereomer having the configuration R*,R*. The remaining diastereomer with the configuration R*,S* comprises the two enantiomers with the configurations R,S and S,R.

The present invention accordingly relates to both the diastereomers of the formula I, having the configuration R*,S*, and the pure enantiomers R,S and S,R of the formula I, which can be separated by conventional methods.

The present invention furthermore relates to mixtures of the diastereomers of the formula I (R*,S*) with the corresponding diastereomers having the configuration R*,R*, with the proviso that the amount of the latter diastereomers in the mixture is less than 50%, in particular less than 30%, based on the total mixture.

In the formula I, examples of the substituents $X_m$ on the phenoxy radical are: hydrogen, 2-fluoro-, 4-fluoro-, 2-chloro-, 3-chloro-, 4-chloro-, 4-bromo-, 2,4-dichloro-, 2,4,6-trichloro-, 3,5-dichloro-, 3-trifluoromethyl-, 4-trifluoromethyl-, 2-prop-1-yl-, 3-(4-chlorophenyl)-, 3-(2-fluorophenoxy)-, 3-(3-chlorophenoxy)-, 4-(3-chlorophenyl) and 3-tert.butoxy-.

Examples of suitable addition salts with acids are the bromides, sulfates, nitrates, phosphates, oxalates and dodecylbenzenesulfonates. The activity of the salts is attributable to the cation, so that the choice of the anion is not critical provided that it is compatible with the substrate or with the plants.

Suitable metal complexes are compounds of the formula III $$Me[(I)_y]Q_x \qquad \text{III,}$$

where I has the above meanings, Me is one equivalent of a metal ion, e.g. copper, zinc, tin, manganese, iron, cobalt or nickel, Q is one equivalent of an anion of an inorganic acid, e.g. hydrochloric acid, sulfuric acid, phosphoric acid or hydrobromic acid, and x and y are the numbers required to balance the valencies.

We have furthermore found that the diastereomeric triazolyl alcohols of the formula I which have an R*,S* configuration are obtained if a ketone of the formula

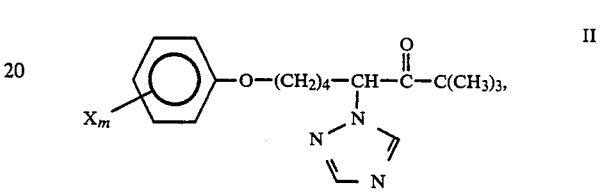

where X and m have the above meanings, is reduced stereo-selectively (a) with a secondary alcoholate or (b) with an alkyl magnesium halide which contains an alkyl radical of 2 to 6 carbon atoms and a beta-hydrogen atom in the alkyl radical, or (c) with hydrogen in the presence of ruthenium or a ruthenium derivative, in particular ruthenium oxide hydroxide (RuO(OH)x).

The resulting alcohols of the formula I contain a substantially higher amount of the diastereomers having an R*,S* configuration than of those having an R*,R* configuration, the amount of the latter diastereomers in the mixture generally being far below 30%. Pure R*,S* diastereomers can be obtained from these simply by washing the crude products with suitable solvents, e.g. diisopropyl ether, or by recrystallization or other conventional purification steps, e.g. chromatography.

In contrast to this, EP-No. 00 40 350 describes specific examples of compounds of the above formula I which consist of diastereomer mixtures R*,R* and R*,S*, which contain very predominant amounts of the R*,R* diastereomers owing to the preparation, the compounds predominantly being prepared from ketones of the formula II with the aid of sodium borohydride.

In the embodiment of the above process, stereo-selective reduction of the stated ketones of the formula II to give the novel R*,S* diastereomers of the formula I is carried out by reacting 1 mole equivalent of these ketones with preferably from 0.3 to 1.5 mole equivalents of a secondary alcoholate, preferably of aluminum, e.g. aluminum isopropylate, aluminum 2-butylate or aluminum cyclohexylate, in the presence of a diluent at 60°–160° C., preferably at the boiling point of the diluent. Suitable diluents are inert organic solvents, in particular alcohols, such as isopropanol or cyclohexanol. The resulting diastereomeric alcoholates are then hydrolyzed to the free alcohols of the formula I in a conventional manner with the aid of an acid.

In the embodiment (b) of the above process, the stereo-selective reduction is carried out by reacting 1 mole equivalent of the ketones of the formula II with an alkyl magnesium halide which contains an alkyl radical of 2 to 6 carbon atoms and has a beta-hydrogen atom in the alkyl radical, preferably with 0.7–1.5 mole equivalents of this halide, in the presence of a diluent at from 0° to 120° C. Examples of suitable alkyl magnesium halides are ethyl magnesium chloride, isopropyl magnesium bromide, n-propyl magnesium bromide and isobutyl magnesium chloride. Preferred solvents for the Grignard reduction are ethers, such as diethyl ether, di-n-propyl ether, tetrahydrofuran or anisole, tertiary amines, such as N,N-diethylaniline, and phosphoric acid tris(dimethylamide). If desired, the reaction can also be carried out in a mixture of these solvents with aliphatic or aromatic hydrocarbons, such as n-hexane or toluene. Depending on the solvent used, the reaction temperature can be varied from 0° to 120° C., temperatures of from 30° to 100° C. being preferred. The magnesium alcoholates initially formed are converted to the alcohols by hydrolysis with water or a dilute aqueous acid, such as hydrochloric acid, sulfuric acid or, preferably, acetic acid, or particularly preferably with aqueous ammonium chloride solution, and, after the aqueous phase has been removed, the alcohols obtained can, if desired, be purified in a conventional manner by extraction, recrystallization or chromatography.

For the stereo-selective reduction in embodiment (c), the catalytic hydrogenation is most advantageously carried out using ruthenium or a ruthenium derivative. This metal may be deposited on an inert carrier, a metal content of from 0.5 to 10% generally being sufficient. In certain cases it may also be possible to use the pure metal, advantageously in a finely divided form. A colloidal ruthenium oxide hydroxide obtained by precipitation from an aqueous ruthenium trichloride solution at pH 8 has proven particularly useful. The oxidic form is converted to the active catalyst under the reaction conditions.

The solvent used is preferably an ether, such as dioxane, tetrahydrofuran or glycol dimethyl ether.

The temperature can be varied within wide limits, temperatures from 100° to 150° C. having proven particularly useful. At these temperatures, the reaction has to be carried out under superatmospheric pressure, from 10 to 30 bar being sufficient. Higher pressures have an adverse effect on the selectivity.

The amount of catalyst is not critical; it depends on the activity, the reaction temperature and the hydrogen partial pressure.

If desired, the compounds of the formula I can also be converted to salts with inorganic or organic acids, for example salts of hydrochloric acid, hydrobromic acid, nitric acid, oxalic acid, acetic acid, sulfuric acid, phosphoric acid or dodecylbenzenesulfonic acid. The activity of the salts is attributable to the cation, so that the choice of the anion is not critical provided that it is compatible with the substrate or with the plants.

The compounds of the formula I can also be converted to metal complexes of the formula III, using a conventional method. This can be done by reacting these compounds with suitable metal salts, e.g. copper(II) chloride, zinc(II) chloride, iron(III) chloride, copper(II) nitrate, manganese(II) chloride or nickel(II) bromide.

The Examples which follow illustrate the preparation of the compounds of the formula I.

EXAMPLE 1

(3-R*,4-S*)-2,2-dimethyl-4-(1,2,4-triazol-1-yl)-8-phenoxy-octan-3-ol (Compound No. 1)

(a) A solution of 12.6 g of 2,2-dimethyl-4-(1,2,4-triazol-1-yl)-8-phenoxyoctan-3-one (cf. German Laid-Open Application DOS No. 3,019,049) in 50 ml of diethyl ether was added dropwise to a stirred solution of 7.4 g of n-propyl magnesium bromide in 30 ml of diethyl ether at the reflux temperature, and, when the addition was complete, the mixture was heated at the stated temperature for a further 3 hours. It was then cooled to 0° C., after which 5 ml of water, followed by 200 ml of 10% strength aqueous ammonium chloride solution, were added dropwise. The organic phase was separated off, dried over magnesium sulfate and evaporated down under reduced pressure. When the residue was boiled up for a short time with 20 ml of diisopropyl ether, 4.0 g of pure compound No. 1 crystallized out in the form of colorless crystals of melting point 132°–133° C.

According to NMR analysis, the mother liquor mainly contained unreacted ketone, together with a little compound No 1 and a very small amount of the R*,R* diastereomer of the compound 1 (mp. 86°–88° C.).

(b) A mixture of 19 g of 2,2-dimethyl-4-(1,2,4-triazol-1-yl)-8-phenoxyoctan-3-one, 7.4 g of aluminum triisopropylate and 115 ml of butan-2-ol was heated in a distillation apparatus at a sufficiently high temperature (about 100° C.) for a distillate (about 5 ml/hour) to pass slowly over. From time to time, depending on the amount distilling over, the boiling mixture was replenished with further butan-2-ol. After 70 hours, NMR analysis showed that at 60% conversion the crude mixture contained, in addition to the starting ketone, the compound No. 1 (R*,S*) and its diastereomer (R*,R*) in a ratio of 7:3.

(c) 280 g of 2,2-dimethyl-4-(1,2,4-triazol-1-yl)-8-phenoxyoctan-3-one were dissolved in 1.8 liters of dioxane, 10 g of RuO(OH)$_x$ were added, and hydrogenation was then carried out in an autoclave for 62 hours under a hydrogen pressure of 25 bar and at 125°. The hydrogenation catalyst was filtered off and the solvent distilled off to give 274 g of residue; according to NMR analysis, this residue contained, in addition to 5% of the starting ketone, the compound No. 1 (R*,S*) and its diastereomer (R*,R*) in a ratio of 7:3. It was possible to isolate the compound No. 1 from the mixture by crystallization from diisopropyl ether.

Examples of diastereomers of the formula I which have an R*,S* configuration and can be prepared in a similar manner are shown in Table 1. The novel R*,S* diastereomers differ from the R*,R* diastereomers (some of which are known) in various chemical and physical properties, for example in the melting points, which are generally higher for the novel R*,S* diastereomers than for the corresponding R*,R* diastereomers (cf. Table 1). When subjected to thin-layer chromatographic analysis using silica gel and a 9:1 mixture of dichloromethane and acetone, the novel R*,S* diastereomers generally prove to be substantially more polar and have a lower $R_f$ value than the corresponding R*,R* diastereomers.

Furthermore, when the $^1$H-NMR spectra are recorded in deuterochloroform, the R*,S* diastereomers all give a signal for the 9 protons of the tert.-butyl group at 0.9–1.0 ppm, whereas the corresponding signal for the R*,R* diastereomers is at 0.7–0.8 ppm. Thus, the proportions of the diastereomers can readily be determined from the corresponding integrated signal intensities in the $^1$H-NMR spectra.

X-ray structure analysis was used to determine the relative configurations of the diastereomers for the examples of compound No. 1 with an R*,S* configuration and the corresponding diastereomers with an R*,R* configuration.

In addition to the novel R*,S* diastereomers, Table 1 also shows some R*,R* diastereomers prepared by reduction with NaBH$_x$, for purposes of comparison (preparation according to Example 2 of EP-No. 00 40 350).

TABLE 1

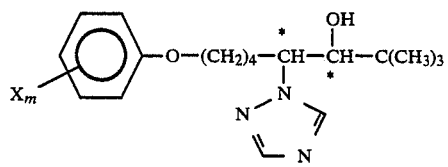

| Compound no. | X$_m$ | R*,S*—Diastereomer % (NMR) | M.p. (°C.) | R*,R*—Diastereomer % (NMR) | M.p.(°C.) | European 40,350 Example |
|---|---|---|---|---|---|---|
| 1 | H | >90% | 132–133 | 90% | 79–81 | 2 |
| 2 | 2-Cl | >95% | 106 | >95% | 98 | — |
| 3 | 2-F | >95% | 89 | >95% | 87 | — |
| 4 | 3-Cl | >95% | 97 | >95% | 90 | — |
| 5 | 4-Cl | >95% | 159 | 90% | 76–78 | 20 |
| 6 | 4-F | >95% | 126–128 | >95% | 86–88 | 77 |
| 7 | 4-CH$_3$ | >95% | 128–130 | >90% | resin | — |
| 8 | 4-methoxy | >95% | 108 | >95% | 89 | — |
| 9 | 3,5-Cl$_2$ | >95% | 122 | — | — | — |
| 10 | 3-CF$_3$ | >95% | 79–83 | — | — | — |
| 11 | 2-CH$_3$ | >95% | 89–93 | — | — | — |
| 12 | 2,6-Cl$_2$ | >95% | 113–116 | — | — | — |
| 13 | 2-methoxy | >95% | 87–88 | — | — | — |
| 14 | 3-CH$_3$ | >95% | 75–79 | — | — | — |
| 15 | 3-methoxy | >95% | 64–67 | — | — | — |
| 16 | 3-phenyl | >95% | 110–111 | — | — | — |
| 17 | 4-phenoxy | >95% | | — | — | — |
| 18 | 3-tert.-butyl | >95% | 59–60 | — | — | — |
| 19 | 3-(1-butoxy)- | >95% | 60–61 | — | — | — |
| 20 | 3-isopropyl | >95% | 73–74 | — | — | — |
| 21 | 4-isopropyl | >95% | 63–66 | — | — | — |
| 22 | 2,4-dichloro | >95% | 106–107 | >90% | 91–93 | 39 |

The advantageous fungicidal action of the diastereomers having R*,S* configuration (referred to in the following as B) over that of the diastereomers having R*,R* configuration (referred to in the following as A) will be apparent from the comparative examples.

COMPARATIVE EXAMPLE 1

Action on *Alternaria Solani* in Tomatoes

Leaves of potted tomatoes of the "Groasse Fleischtomate" variety cultivated in the greenhouse were sprayed at the 4-leaf stage with aqueous suspensions containing (dry basis) 80% of active ingredient and 20% of emulsifier. After the sprayed-on layer had dried, the leaves were inoculated with an aqueous spore suspension of the fungus *Alternaria solani*. The plants were then placed for 4 days in a water vapor-saturated chamber kept at 22° to 24° C. After this period, the disease had spread on the untreated control plants to such a considerable extent that the fungicidal action of the compounds was able to be assessed.

| Scale: 0 = no fungus attack, graded down to 5 = total attack | |
|---|---|
| Active ingredient no. (= Compound no.) | Leaf attack after spraying with 0.5% liquor |
| 2 Diastereomer B | 0 |
| Corresponding diastereomer A | 1 |
| 3 Diastereomer B | 0 |
| Corresponding diastereomer A | 2 |
| 4 Diastereomer B | 1 |
| Corresponding diastereomer A | 3 |
| 7 Diastereomer B | 1 |
| Corresponding diastereomer A | 3 |
| 10 Diastereomer | 1 |
| Corresponding diastereomer A | 3 |
| 11 Diastereomer B | 0 |
| Corresponding diastereomer A | 2 |
| 13 Diastereomer B | 1 |
| Corresponding diastereomer A | 3–4 |
| Untreated | 5 |

COMPARATIVE EXAMPLE 2

Action on *Botrytis cinerea* in Pimientos

Pimiento seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus *Botrytis cinerea*, and placed at 22° to 24° C. in a chamber of high humidity. After 5 days, the disease had spread to such a great extent on the untreated plants that the necroses covered the major portion of the leaves.

| Active ingredient no. (= Compound no.) | Scale: 0 = no fungus attack, graded down to 5 = total attack | | | |
|---|---|---|---|---|
| | Leaf attack after spraying with liquor containing active ingredient in amounts of | | | |
| | 0.05% | 0.025% | 0.0125% | 0.006% |
| 2 Diastereomer B | 0 | 0 | 0 | 0 |
| Corresponding diastereomer A | 0 | 1 | 1 | 3 |
| 3 Diastereomer B | 0 | 0 | 0 | 0 |
| Corresponding diastereomer A | 0 | 0 | 1 | 1 |
| 4 Diastereomer B | 0 | 0 | 0 | 0 |
| Corresponding diastereomer A | 0 | 1 | 2 | 2 |
| 7 Diastereomer B | 0 | 0 | 0 | 0 |
| Corresponding diastereomer A | 0 | 1 | 4 | 5 |
| 11 Diastereomer B | 0 | 0 | 0 | 1 |
| Corresponding diastereomer A | 5 | 4 | 5 | 5 |
| 14 Diastereomer B | 0 | 1 | 0 | 1 |
| Corresponding diastereomer A | 2 | 1 | 1 | 4 |
| 15 Diastereomer B | 0 | 1 | 2 | 5 |
| Corresponding diastereomer A | 5 | 5 | 5 | 5 |
| 22 Diastereomer B | 0 | 1 | 1 | 1 |
| Corresponding diastereomer A | 3 | 2 | 4 | 4 |
| Untreated | | 5 | | |

COMPARATIVE EXAMPLE 3

Action on Leaf Rust on Wheat

Leaves of pot-grown wheat seedlings of the "Jubilar" variety were dusted with spores of rust (*Puccinia recondita*). The pots were than placed in a high humidity (90–95%) chamber at from 20° to 22° C. for 24 hours. During this time, the spores germinated and the germ tubes penetrated into the leaf tissue. The infected plants were then sprayed to run-off with aqueous liquors, the solids comprising 80% of active ingredient and 20% of emulsifier. After the spray coating had dried, the test plants were set up in a greenhouse at from 20° to 22° C. and from 65 to 70% relative humidity. After 8 days, the degree of development of the rust fungi on the leaves was determined.

| Active ingredient no. (= Compound no.) | Scale: 0 = no fungus attack, graded down to 5 = total attack | |
|---|---|---|
| | Leaf attack after spraying with liquor containing active ingredient in amounts of | |
| | 0.025% | 0.006% |
| 10 Diastereomer B | 0 | 0 |
| Corresponding diastereomer A | 0 | 1 |
| 11 Diastereomer B | 0 | 2 |
| Corresponding diastereomer A | 2 | 4 |
| 13 Diastereomer B | 1 | 3–4 |
| Corresponding diastereomer A | 4 | 4 |
| 14 Diastereomer B | 0 | 0 |
| Corresponding diastereomer A | 1 | 3–4 |
| 15 Diastereomer B | 0 | 3 |
| Corresponding diastereomer A | 4 | 4 |
| Untreated | 4–5 | |

The compounds having the configuration according to the invention are applied as fungicidal active ingredients, especially for crop protection, by spraying or dusting substrates or plants with them, or treating plant seed with them. Application may be effected before or after infection of the plants or seed by the fungi.

The compounds according to the invention may be converted into the usual formulations, e.g. solutions, emulsions, suspensions, dusts, powders, pastes and granules. The forms of application depend entirely on the purpose for which the agents are being used, but they must ensure a fine and uniform distribution of the active ingredients. The formulations are prepared in conventional manner, e.g., by extending the active ingredient with solvents and/or carriers, if desired using emulsifiers and dispersants. Where water is used as diluent, other organic solvents may also be employed as auxiliary solvents. Suitable compounds for preparing such formulations are solvents such as aromatics (e.g., xylene, benzene), chlorinated aromatics (e.g., chlorobenzenes), paraffins (e.g., petroleum fractions), alcohols (e.g., methanol, butanol), ketones (e.g., cyclohexanone), amines (e.g., ethanolamine, dimethylformamide), and water; carriers such as natural rock flours (e.g., kaolins, diatomaceous earth, talc, chalk) and synthetic rock flours (e.g., highly disperse silicic acid, silicates); emulsifiers such as nonionic and anionic emulsifying agents (e.g. polyoxyethylene-fatty alcohol ethers, alkyl sulfonates and aryl sulfonates); and dispersants such as lignin, sulfite waste liquors and methyl cellulose.

The formulations generally contain from 0.1 to 95, and preferably from 0.5 to 90, wt % of active ingredient.

The application rates depend on the effect desired, and range from 0.02 to 3 kg/ha and more. The active ingredients may also be used for protecting materials, e.g., for combatting wood-destroying fungi such as *Coniophora puteana* and *Polystictus versicolor*. The active ingredients may be employed as fungicidally effective components of oily wood preservatives for protecting wood against wood-discoloring fungi. The agents are applied by treating, e.g., impregnating or painting, the wood with them.

The formulations and the ready-to-use products made therefrom, e.g., solutions, emulsions, suspensions, powders, dusts, pastes or granules, are applied in known manner, for example by spraying, atomizing, dusting, scattering, seed-disinfecting, or watering.

Examples of formulations are given below.

I. 90 parts by weight of compound no. 2 is mixed with 10 parts by weight of N-methyl-alpha-pyrrolidone. A mixture is obtained which is suitable for application in the form of very fine drops.

II. 20 parts by weight of compound no. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 3 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into water and finely distributing it therein, an aqueous dispersion is obtained.

IV. 20 parts by weight of compound no. 4 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 7 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 2 is intimately mixed with 97 parts by weight of particulate kaolin. A dust is obtained containing 3% by weight of the active ingredient.

VII. 30 parts by weight of compound no. 3 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 4 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts of compound no. 7 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

In these application forms, the agents according to the invention may also be mixed and applied with other active ingredients, e.g., herbicides, insecticides, growth regulators, other fungicides and fertilizers. When mixed with other fungicides, the spectrum of fungicidal action is in many cases increased. The following list of fungicides with which the compounds according to the invention may be combined is intended to illustrate and not restrict the combination possibilities:
sulfur
dithiocarbamates and derivatives thereof, such as
ferric dimethyldithiocarbamate
zinc dimethyldithiocarbamate
manganese ethylenebisdithiocarbamate
zinc ethylenebisthiocarbamate
tetramethylthiuram disulfide
manganese-zinc ethylenediamine-bisdithiocarbamate
zinc-(N,N'-propylene-bisdithiocarbamate)
ammonia complex of zinc-(N,N'-ethylene)-bisdithiocarbamate and
N,N'-polyethylene-bis-(thiocarbamoyl)-disulfide
ammonia complex of zinc-(N,N'-propylene-bisdithiocarbamate) and
N,N'-polypropylene-bis-(thiocarbamoyl)-disulfide nitro derivatives, such as
dinitro-(1-methylheptyl)-phenylcrotonate
2-sec-butyl-4,6-dinitrophenyl-3,5-dimethylacrylate
2-sec-butyl-4,6-dinitrophenylisopropylcarbonate
diisopropyl 5-nitroisophthalate
heterocyclic structures, such as
2-heptadecyl-2-imidazoline acetate
2,4-dichloro-6-(o-chloroanilino)-s-triazine
O,O-diethylphthalimidophosphorothionate
5-amino-1-[bis-(dimethylamino)-phosphynyl-]3-phenyl-1,2,4-triazole
2,3-dicyano-1,4-dithiaanthraquinone
2-thio-1,3-dithio-(4,5-b)-quinoxaline
methyl 1-(butylcarbamoyl)-2-benzimidazole carbamate
2-methoxycarbonylaminobenzimidazole
2-[furyl-(2)]-benzimidazole
2-[thiazolyl-(4)]-benzimidazole
N-(1,1,2,2-tetrachloroethylthio)-tetrahydrophthalimide
N-trichloromethylthiotetrahydrophthalimide
N-trichloromethylphthalimide
N-dichlorofluoromethylthio-N',N'-dimethyl-N-phenyl-sulfuric acid diamide
5-ethoxy-3-trichloromethyl-1,2,3-thiadiazole
2-thiocyanomethylthiobenzthiazole
1,4-dichloro-2,5-dimethoxybenzole
4-(2-chlorophenylhydrazono)-3-methyl-5-isoxazolone
pyridine-2-thio-1-oxide
8-hydroxyquinoline and its copper salt
2,3-dihydro-5-carboxanilido-6-methyl-1,4-oxathiin
2,3-dihydro-5-carboxanilido-6-methyl-1,4-oxathiin-4,4-dioxide
2-methyl-5,6-dihydro-4-H-pyran-3-carboxanilide
2-methyl-furan-3-carboxanilide
2,5-dimethyl-furan-3-carboxanilide
2,4,5-trimethyl-furan-3-carboxanilide
2,5-dimethyl-furan-3-carboxylic acid cyclohexylamide
N-cyclohexyl-N-methoxy-2,5-dimethyl-furan-3-carboxamide
2-methyl-benzoic acid anilide
2-iodobenzoic anilide
N-formyl-N-morpholine-2,2,2-trichloroethylacetal
piperazine-1,4-diylbis-(1-(2,2,2-trichloroethyl)-formamide
1-(3,4-dichloroanilino)-1-formylamino-2,2,2-trichlorethane
2,6-dimethyl-N-tridecyl-morpholine and its salts
2,6-dimethyl-N-cyclododecyl-morpholine and its salts
N-[3-(p tert.-butylphenyl)-2-methylpropyl-]-cis-2,6-dimethylmorpholine
N-[3-(p-tert.-butylphenyl)-2-methylpropyl]-piperidine
1-[2-(2,4-dichlorophenyl)-4-ethyl-1,3-dioxolan-2-yl-ethyl]-1-H-1,2,4-triazole
1-[2-(2,4-dichlorophenyl)-4-n-propyl-1,3-dioxolan-2-yl-ethyl]-1-H-1,2,4-triazole
N-(n-propyl)-N-(2,4,6-trichlorophenoxyethyl)-N'-imidazolylurea
1-(4-chlorophenoxy)-3,3-dimethyl-1-(1H-1,2,4-triazol-1-yl)-2-butanone
1-(4-chlorophenoxy)-3,3-dimethyl-1-(1H-1,2,4-triazol-1-yl)-2-butanol alpha-(2-chlorophenyl)-alpha-(4-chlorophenyl)-5-pyrimidinemethanol
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene
1,2-bis-(3-methoxycarbonyl-2-thioureido)-benzene and various substances, such as
dodecylguanidine acetate
3-[2-(3,5-dimethyl-2-oxycyclohexyl)-2-hydroxyethyl]-glutarimide
hexachlorobenzene
D,L-methyl-N-(2,6-dimethylphenyl)-N-(2-furoyl)-alanate
methyl D,L-N-(2,6-dimethylphenyl)-N-(2-methoxyacetyl)-alanate
N-(2,6-dimethylphenyl)-N-chloroacetyl-D,L-2-aminobutyrolactone
methyl DL-N-(2,6-dimethylphenyl)-N-(phenylacetyl)-alanate
5-methyl-5-vinyl-3-(3,5-dichlorophenyl)-2,4-dioxo-1,3-oxazolidine
3-(3,5-dichlorophenyl)-5-methyl-5-methoxymathyl-1,3-oxazolidin-2,4-dione
3-(3,5-dichlorophenyl)-1-isopropyl-carbamoylhydantoin
N-(3,5-dichlorophenyl)-1,2-dimethyl-cyclopropane-1,2-dicarboximide.

The compounds according to the invention, and their salts and metal complex compounds, have an excellent action on a broad spectrum of plant-pathogenic fungi, especially from the Ascomycetes, Basidiomycetes and Deuteromycetes classes. Some of them have a systemic action and may be used as soil and foliar fungicides.

The fungicidal compounds are of particular interest for combating a large number of fungi in various crops or their seed, especially wheat, rye, barley, oats, rice, Indian corn, cotton, soybeans, coffee, sugarcane, fruit, ornamentals in horticulture, and vegetables, such as cucumbers, beans and Cucurbitaceae.

The novel compounds are particularly suitable for combating the following diseases: *Erysiphe graminis* in cereals, *Erysiphe cichoriacearum* in Cucurbitaceae, *Podosphaera leucotricha* in apples, *Uncinula necator* in grapes, Puccinia species in cereals, *Rhizoctonia solani* in cotton, Ustilago species in cereals and sugarcane, *Venturia inaequalis* (apple scab), *Septoria nodorum* in wheat, *Botrytis cinerea* in grapes and strawberries, *Cercospora musae* in bananas, *Pseudocercosporella herpotrichoides* in wheat and barley, *Hemileia vastatrix* in coffee, *Piricularia oryzae* in rice, and *Alternaria solani* in potatoes and tomatoes.

The compounds according to the invention are particularly effective on Botrytis and Alternaria.

We claim

1. A method for the production of the diastereomeric triazolyl alcohols of the formula

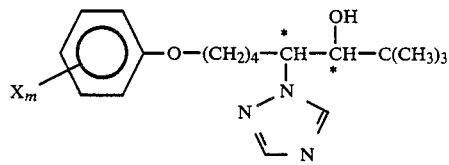

where X is hydrogen, halogen, trifluoromethyl, $C_1$–$C_4$-alkyl, $C_1$–$C_4$-alkoxy, unsubstituted or substituted phenyl or unsubstituted or substituted phenoxy wherein the substitute on the phenyl or the phenoxy is halogen and m is an integer from 1 to 5, x being identical or different when m is greater than 1, which, as diastereomers, have the R*,S* configuration at the two chiral centers, and the enantiomers which have the configuration R,S or S,R at the two chiral centers, and their acid addition salts and metal complexes, which comprises reducing stereo-selectively the corresponding ketone of the above formula with, (a) an alkyl magnesium halide which contains an alkyl radical of 2–6 carbon atoms and a beta-hydrogen atom in the alkyl radical or, (b) hydrogen in the presence of ruthenium or ruthenium oxide hydroxide ($Ru(OH)_x$).

2. A process of claim 1 wherein X is a member selected from the group consisting of 2-Cl; 2-F; 3-Cl; 4-$CH_3$; 4-methoxy; 3,5-$Cl_2$; 3-$CF_3$; 2-$CH_3$; 2,6$Cl_2$; 2-methoxy; 3-$CH_3$; 3-methoxy; 3-phenyl; 4-phenoxy; 3-tert.-butyl; 3-(1-butoxy); 3-isopropyl; and 4-isopropyl.

3. A process of claim 1 wherein X is 2-F.

* * * * *